US012734204B2

(12) United States Patent
Choi

(10) Patent No.: US 12,734,204 B2
(45) Date of Patent: Sep. 15, 2026

(54) **COMPOSITION FOR ANTI-OBESITY AND PREVENTING OR TREATING MUSCLE LOSS, CONTAINING CATECHIN GLYCOSIDE EXTRACT DERIVED FROM PLANT IN GENUS *Ulmus* AS ACTIVE INGREDIENT**

(71) Applicant: DR. OREGONIN INC., Chuncheon-si (KR)

(72) Inventor: Sun Eun Choi, Chuncheon-si (KR)

(73) Assignee: DR. OREGONIN INC., Chuncheon-si (KR)

( * ) Notice: Subject to any disclaimer, the term of this patent is extended or adjusted under 35 U.S.C. 154(b) by 431 days.

(21) Appl. No.: 18/266,174

(22) PCT Filed: May 10, 2022

(86) PCT No.: PCT/KR2022/006674
§ 371 (c)(1),
(2) Date: Jun. 8, 2023

(87) PCT Pub. No.: WO2023/158020
PCT Pub. Date: Aug. 24, 2023

(65) Prior Publication Data

US 2024/0382544 A1 Nov. 21, 2024

(30) Foreign Application Priority Data

Feb. 21, 2022 (KR) ........................ 10-2022-0021852
Mar. 25, 2022 (KR) ........................ 10-2022-0037112

(51) Int. Cl.

| | |
|---|---|
| ***A61K 36/185*** | (2006.01) |
| ***A61P 3/04*** | (2006.01) |
| ***A61P 21/00*** | (2006.01) |

(52) U.S. Cl.
CPC .............. *A61K 36/185* (2013.01); *A61P 3/04* (2018.01); *A61P 21/00* (2018.01); *A61K 2236/33* (2013.01); *A61K 2236/37* (2013.01)

(58) Field of Classification Search
CPC .............. A61K 36/185; A61K 2236/33; A61K 2236/37; A61P 3/04; A61P 21/00
See application file for complete search history.

(56) References Cited

U.S. PATENT DOCUMENTS 6,045,800 A * 4/2000 Kim ....................... A61Q 11/00
424/769

FOREIGN PATENT DOCUMENTS

| | | | | |
|---|---|---|---|---|
| KR | 101213519 B1 | 12/2012 | | |
| KR | 20130060806 A | * 6/2013 | ................ A61P 3/04 |
| KR | 20140145666 A | 12/2014 | | |
| KR | 20190070487 A | 6/2019 | | |
| KR | 102238793 B1 | 4/2021 | | |
| KR | 20210087406 A | 7/2021 | | |
| KR | 102345933 B1 | 1/2022 | | |

OTHER PUBLICATIONS

English Espacenet Translation of KR 2013 0060806 A (34 pages), published Jun. 10, 2013. (Year: 2013).*
Jeon et al., "Effect of melanin reduction by extracts from Ulmus davidiana by supercritical fluid extraction," Toxicology and Environmental Health Sciences (2020) 12:325-329. (Year: 2020).*
International search report of PCT/KR2022/006674, Nov. 14, 2022.

* cited by examiner

*Primary Examiner* — Aradhana Sasan
(74) *Attorney, Agent, or Firm* — STIP Law Group, LLC

(57) ABSTRACT

Provided is a pharmaceutical composition for anti-obesity and preventing or treating muscle loss, which contains an extract of a plant in the genus *Ulmus* as an active ingredient.

9 Claims, 16 Drawing Sheets

【FIG. 1】
Extraction diagram
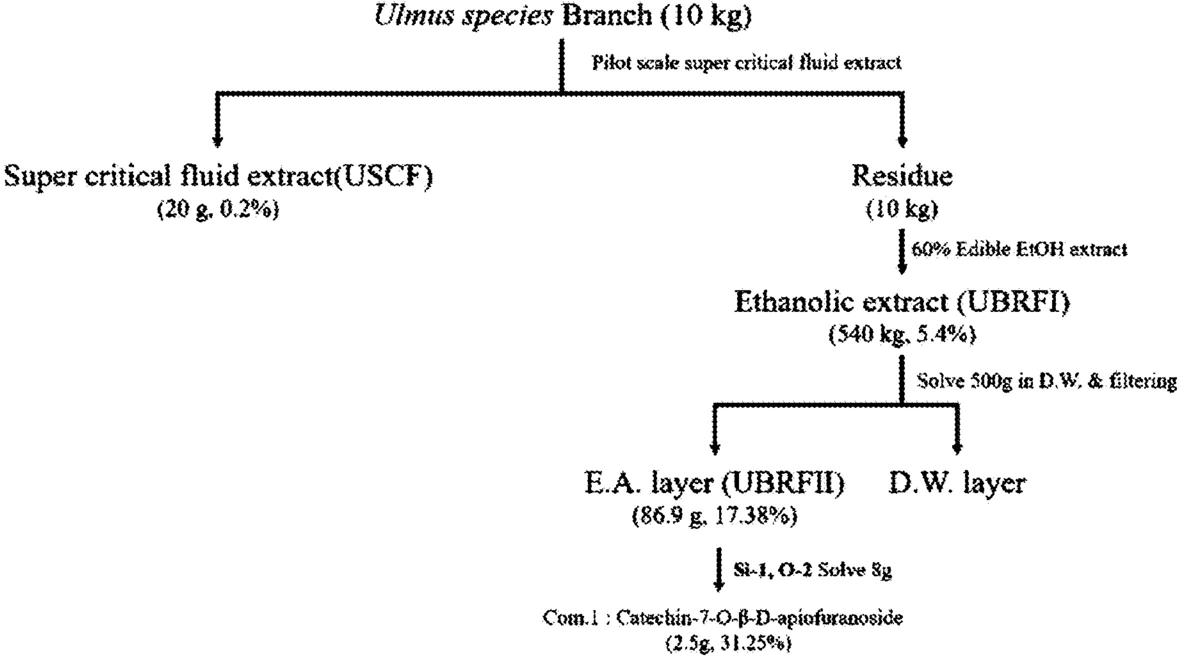
【FIG. 2】
Extraction diagram
*Ulmus species* Root (6.45 kg)
60% Edible EtOH extract, room temp
Ethanolic extract (UR)
(392g, 6.07%)

【FIG. 3】
Extraction diagram
*Ulmus species* Branch (10 kg)
↓ 60% Edible EtOH extract, room temp
Ethanolic extract (U60E)
(429g, 4.29%)
【FIG. 4】
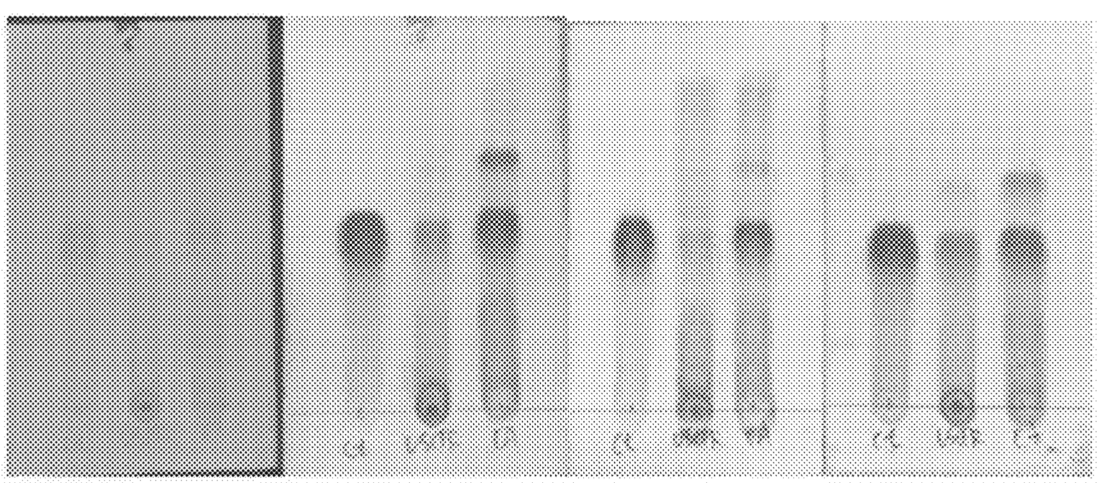
UV lamp:254nm FeCl$_3$ 10% $H_2SO_4$ p-Anisaldehyde$H_2SO_4$ 【FIG. 5】
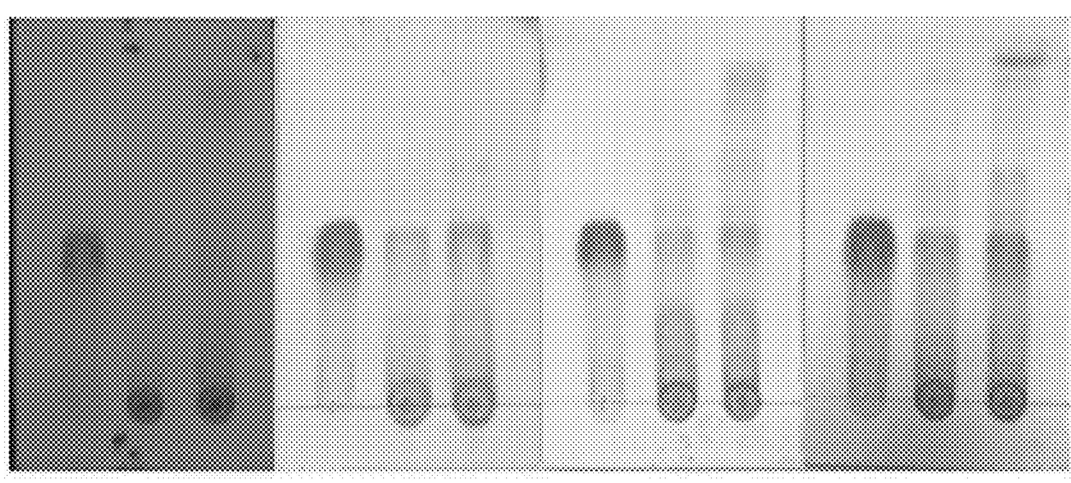
UV lamp:254nm FeCl$_3$ 10% $H_2SO_4$ p-Anisaldehyde$H_2SO_4$ 【FIG. 6】
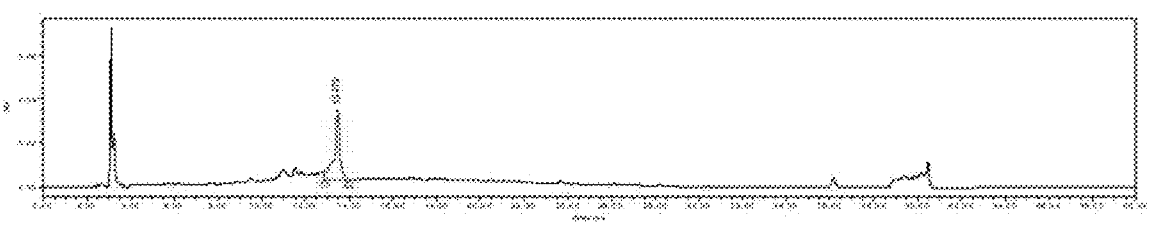
[UR HPLC chromatogram, Contents: 62.67 μg/ml]
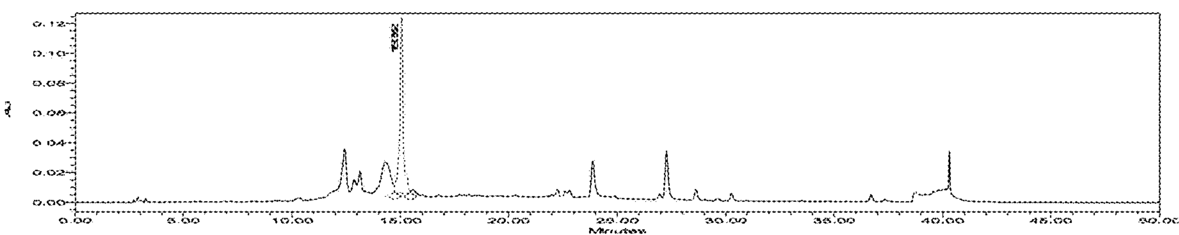
[UBC HPLC chromatogram, Contents: 144.94 μg/ml]
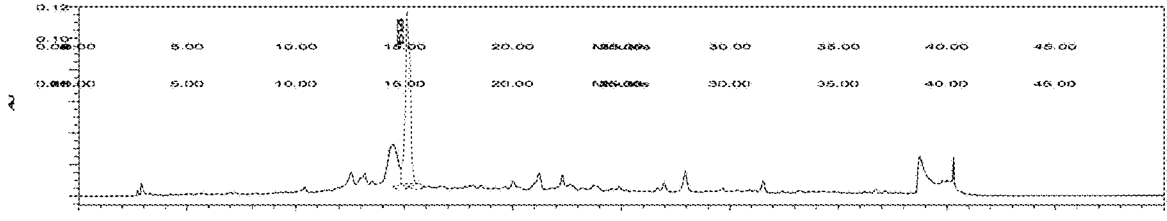
[UBRF-I HPLC chromatogram, Contents: 192.28 μg/ml]
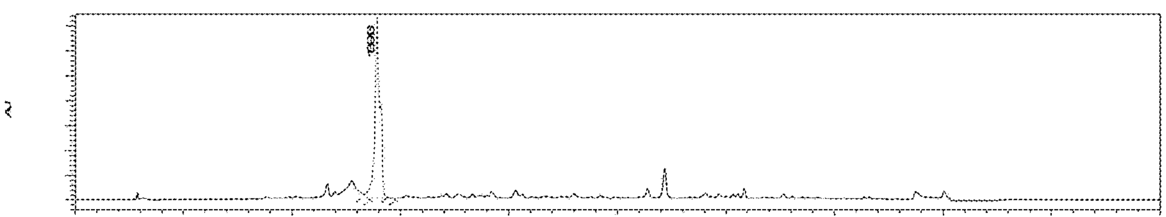
[UBRF-II HPLC chromatogram, Contents: 655.31 μg/ml]

【FIG. 7】
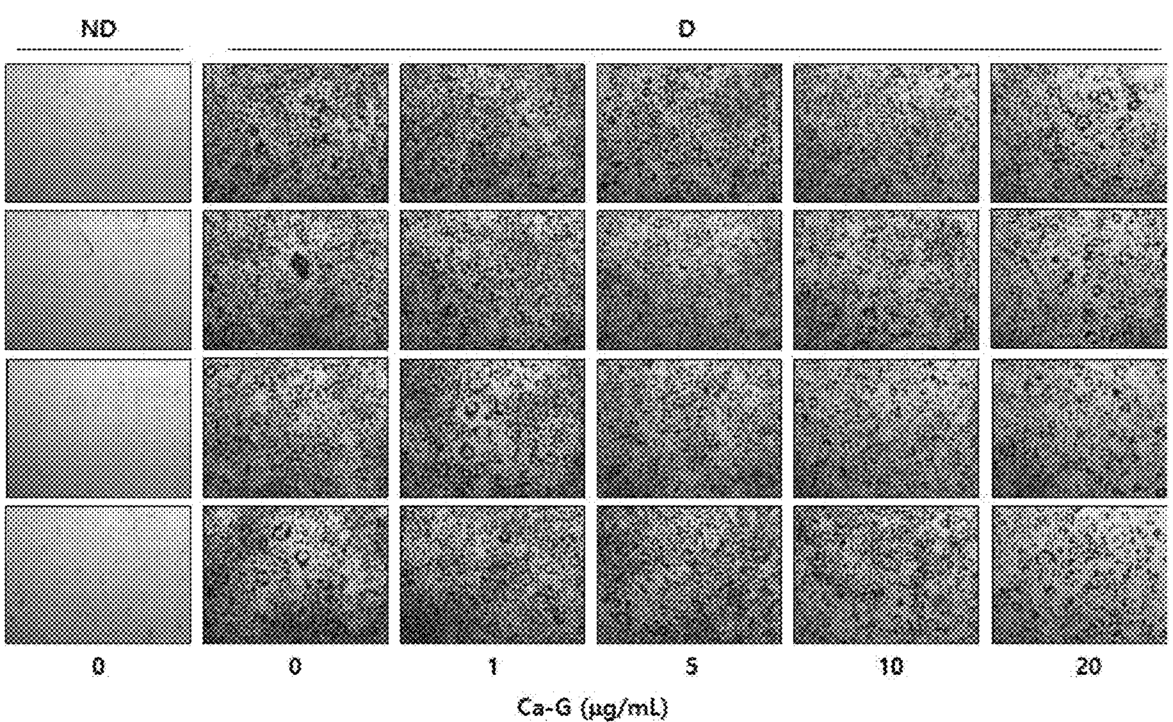
【FIG. 8】
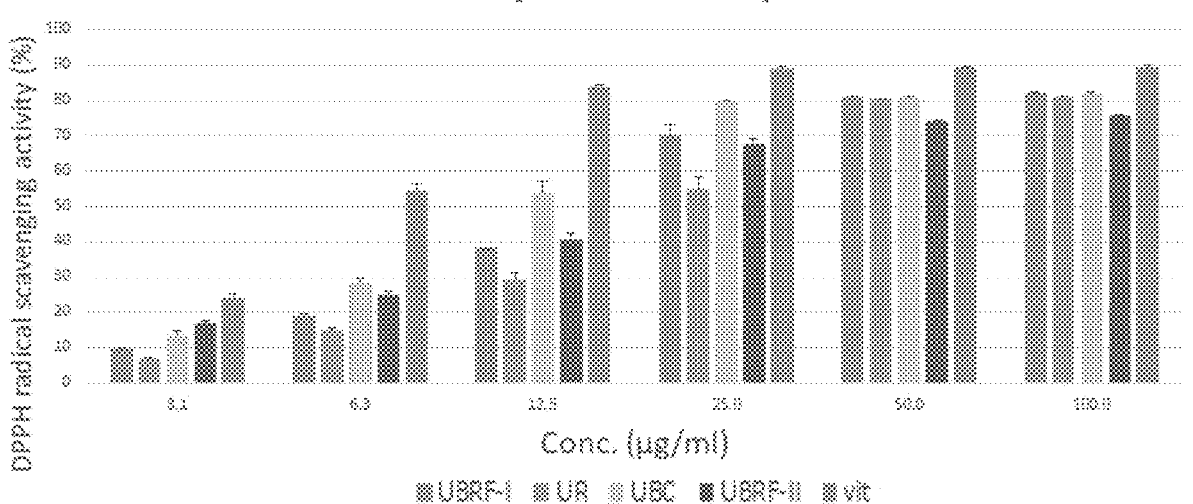

【FIG. 9】
| IC50 | | | | |
|---|---|---|---|---|
| UBRF-I | UR | UBC | UBRF-II | vit |
| 17.5±0.59 | 22.62±1.45 | 11.57±0.68 | 17.17±0.67 | 5.80±0.18 |
【FIG. 10】
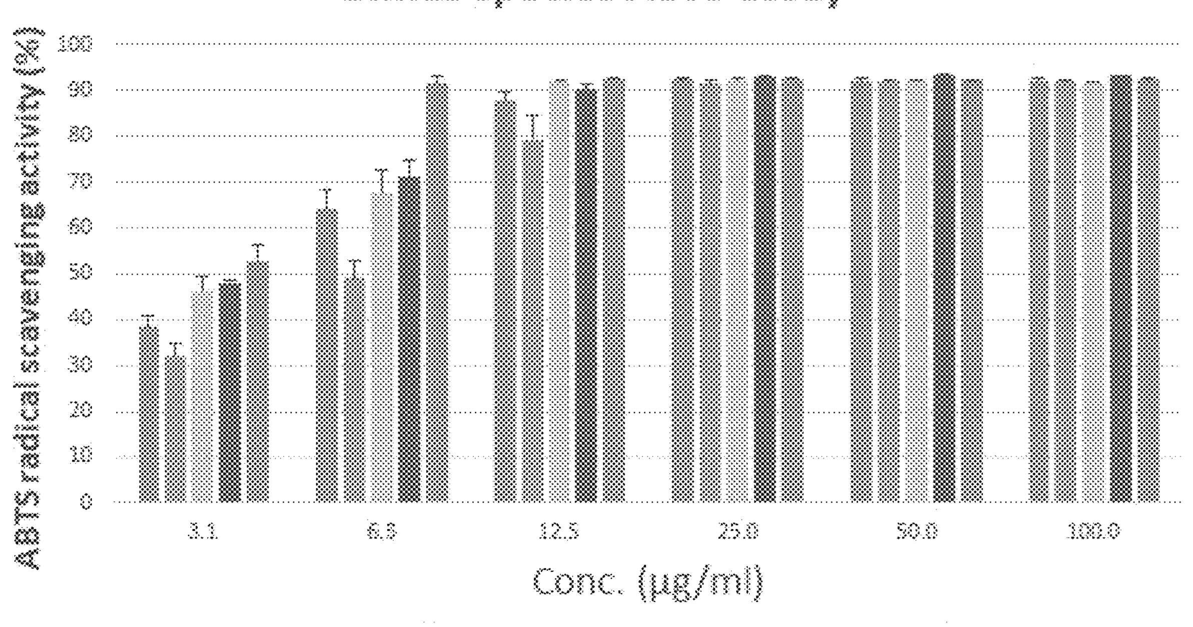

【FIG. 11】
| IC50 | | | | |
|---|---|---|---|---|
| UBRF-I | UR | UBC | UBRF-II | vit |
| 4.77±0.52 | 6.61±0.73 | 3.43±0.74 | 3.44±0.13 | 2.62±0.50 |
【FIG. 12】
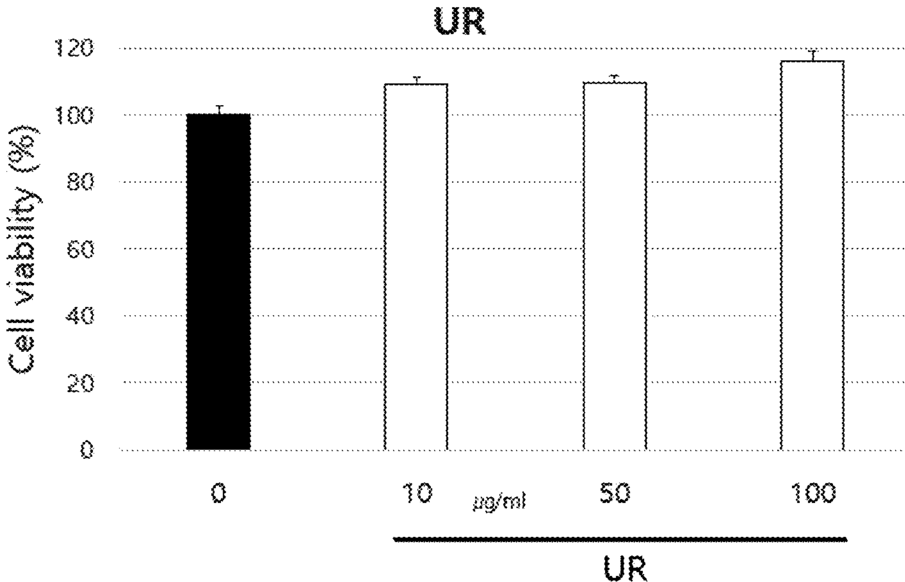

【FIG. 13】
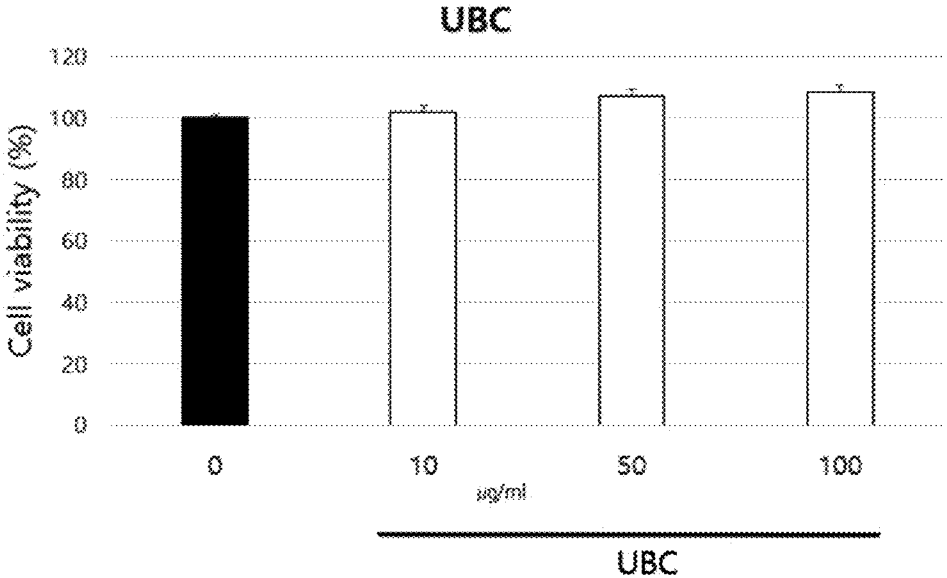
【FIG. 14】
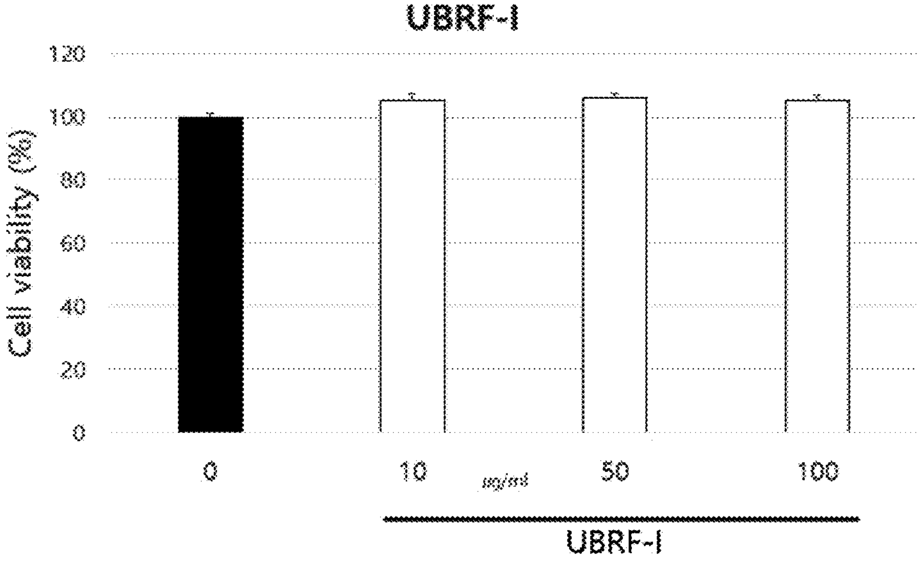

【FIG. 15】
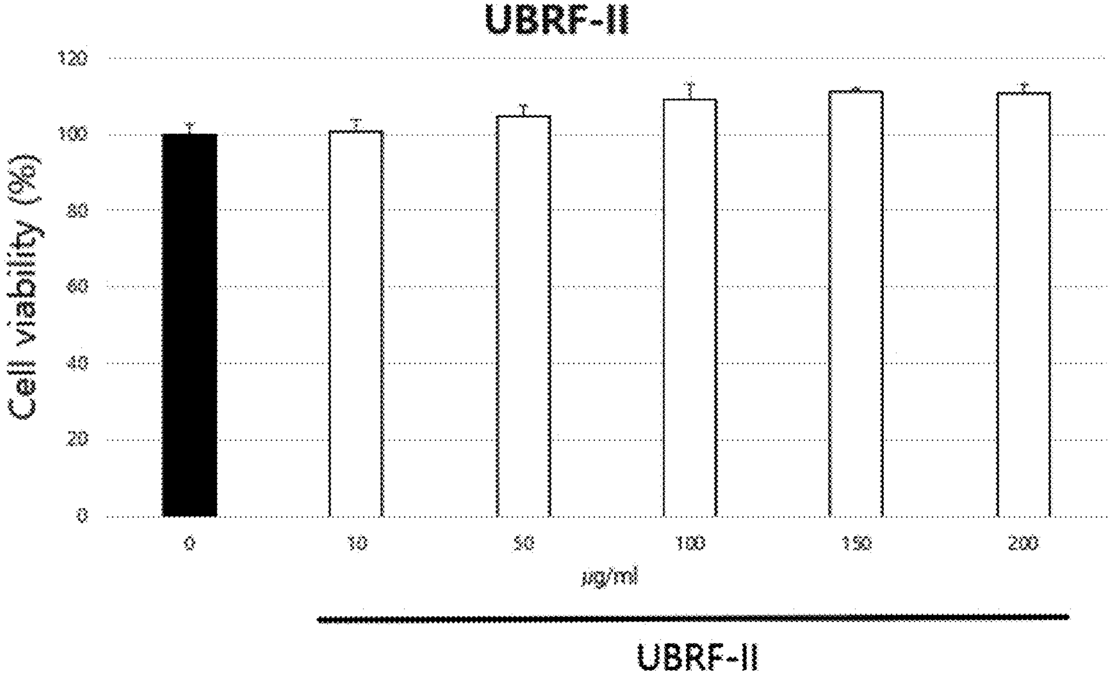
【FIG. 16】
| | UR | UBC | UBRF-I | UBRF-II |
|---|---|---|---|---|
| 0 μg/mL | 100.0 ± 2.8 | 100.0 ± 0.9 | 100.0 ± 1.2 | 100.0 ± 2.6 |
| 10 μg/mL | 109.1 ± 2.3 | 101.8 ± 2.2 | 105.3 ± 2.1 | 100.5 ± 3.6 |
| 50 μg/mL | 109.6 ± 2.1 | 107.3 ± 1.9 | 105.9 ± 1.3 | 104.8 ± 2.8 |
| 100 μg/mL | 116.1 ± 3.0 | 108.6 ± 1.9 | 105.2 ± 1.7 | 109.1 ± 4.0 |
| 150 μg/mL | - | - | - | 111.1 ± 0.7 |
| 200 μg/mL | - | - | - | 110.7 ± 2.3 |

【FIG. 17】
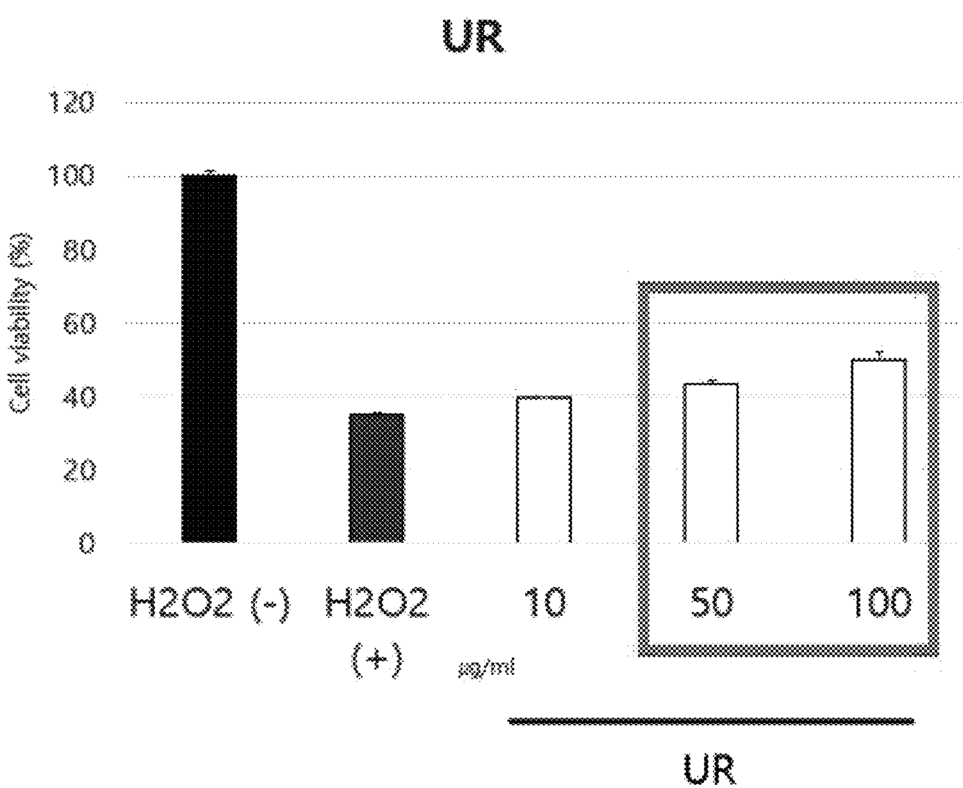

【FIG. 18】
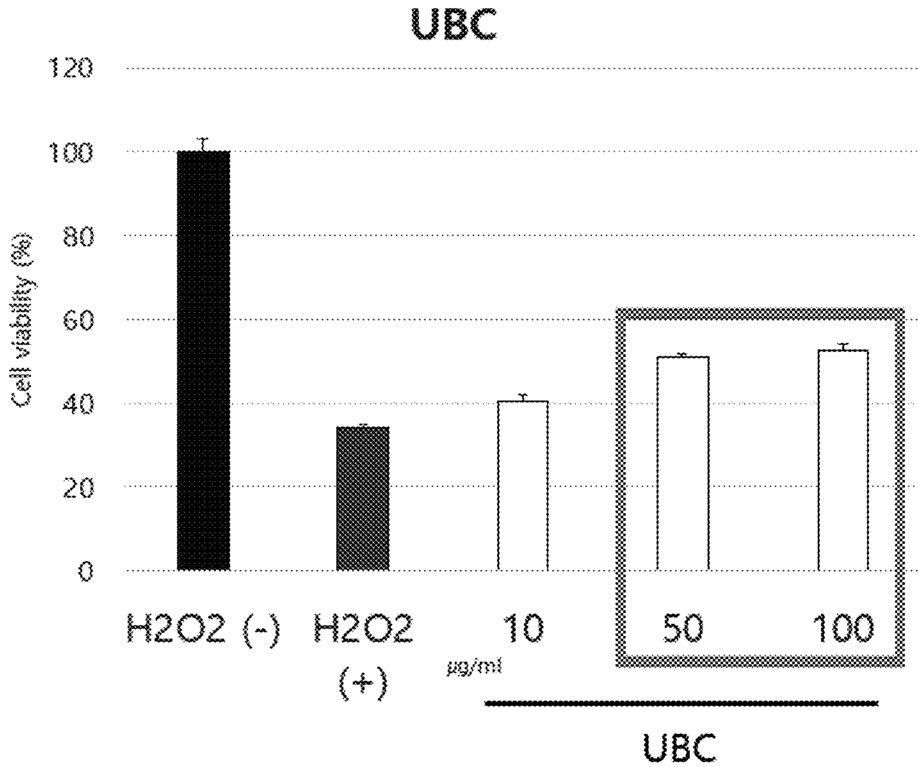

【FIG. 19】
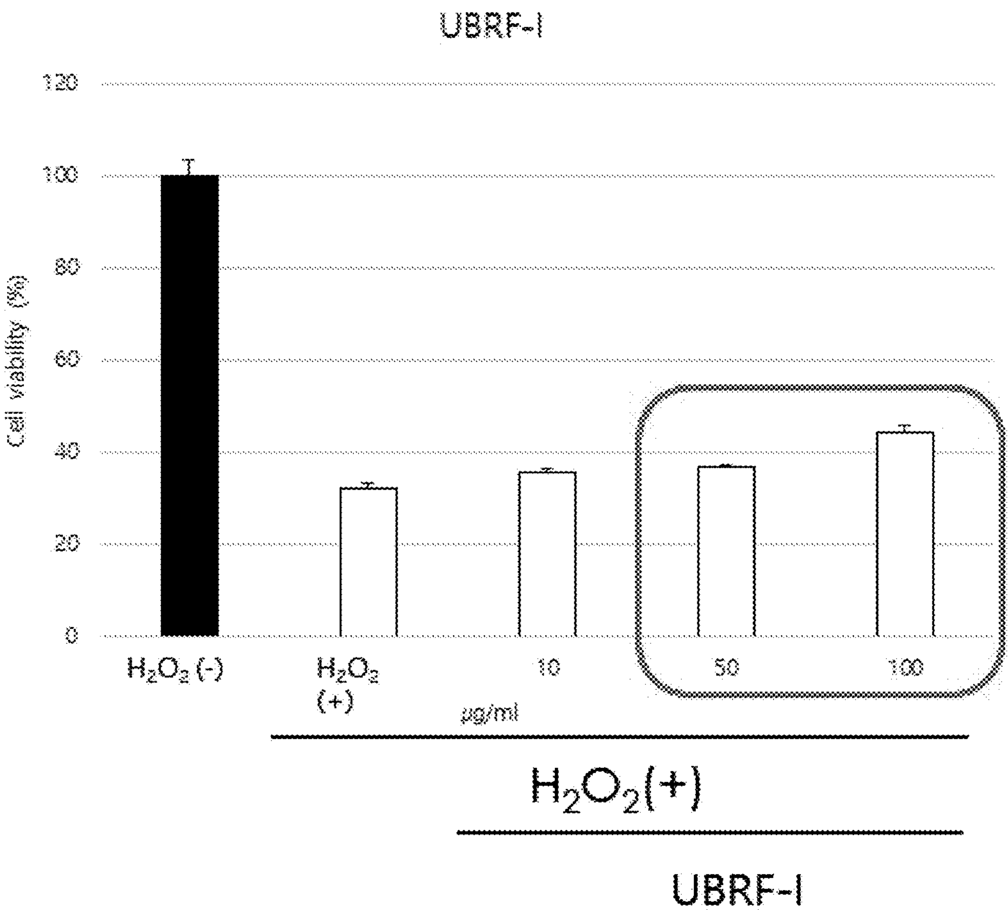

【FIG. 20】
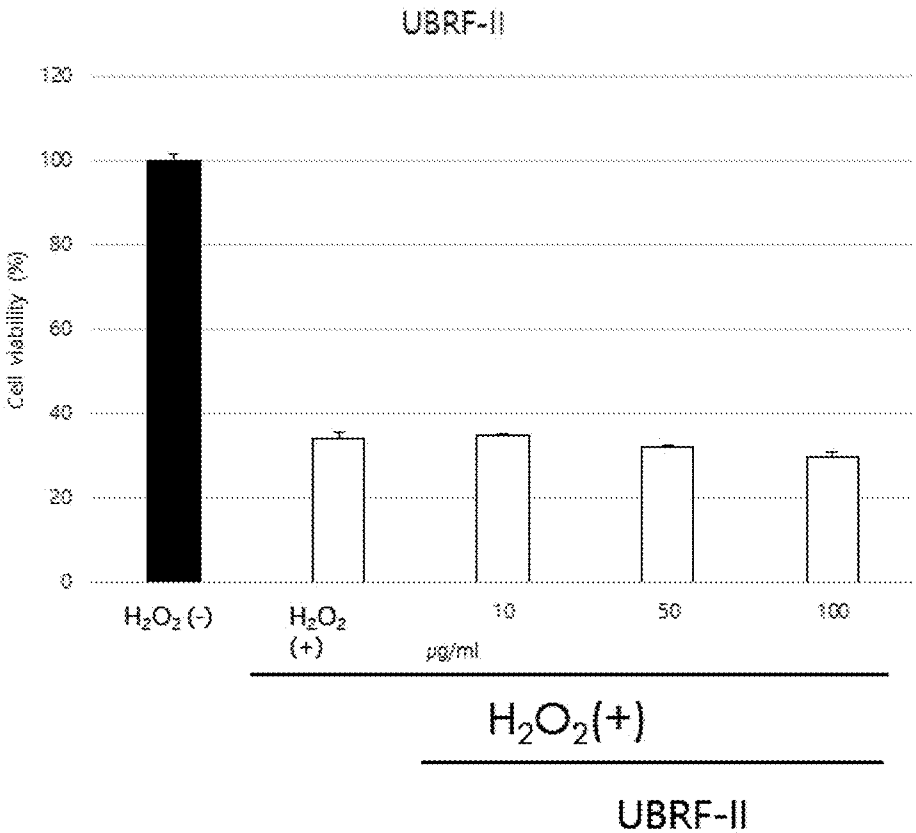
【FIG. 21】
| | | UR | UBC | UBRF-I | UBRF-II |
|---|---|---|---|---|---|
| $H_2O_2$ (-) | (-) | 100.0 ± 1.3 | 100.0 ± 3.0 | 100.0 ± 3.4 | 100.0 ± 1.6 |
| $H_2O_2$ (+) | (-) | 34.9 ± 0.7 | 34.1 ± 0.9 | 31.9 ± 1.2 | 33.9 ± 1.7 |
| $H_2O_2$ (+) | 10 μg/mL | 39.7 ± 0.1 | 40.7 ± 1.3 | 35.5 ± 0.8 | 35.0 ± 0.4 |
| $H_2O_2$ (+) | 50 μg/mL | 43.4 ± 0.8 | 50.9 ± 0.9 | 36.6 ± 0.7 | - |
| $H_2O_2$ (+) | 100 μg/mL | 49.8 ± 2.5 | 52.6 ± 1.6 | 44.1 ± 1.7 | - |

【FIG. 22】
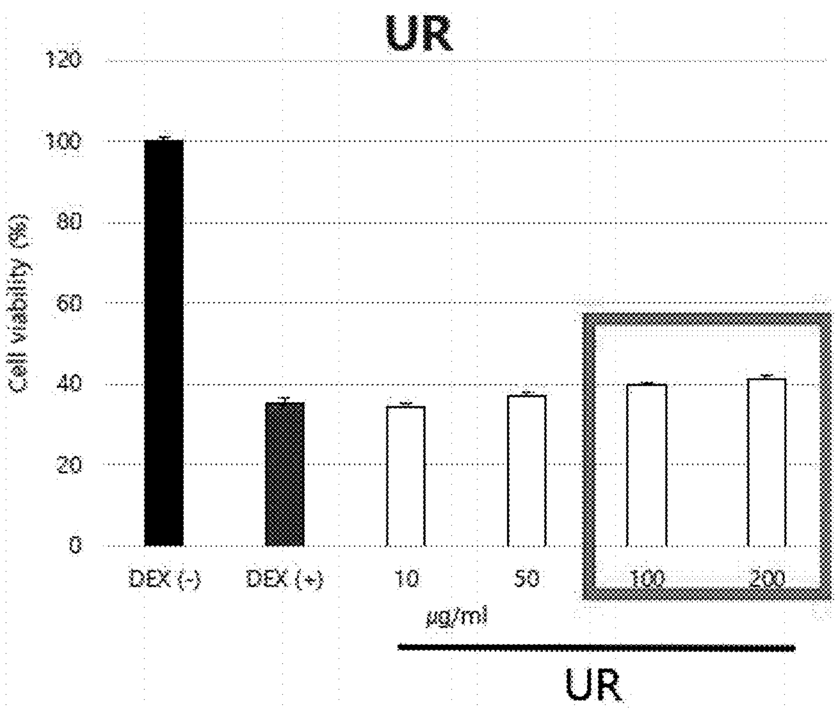
【FIG. 23】
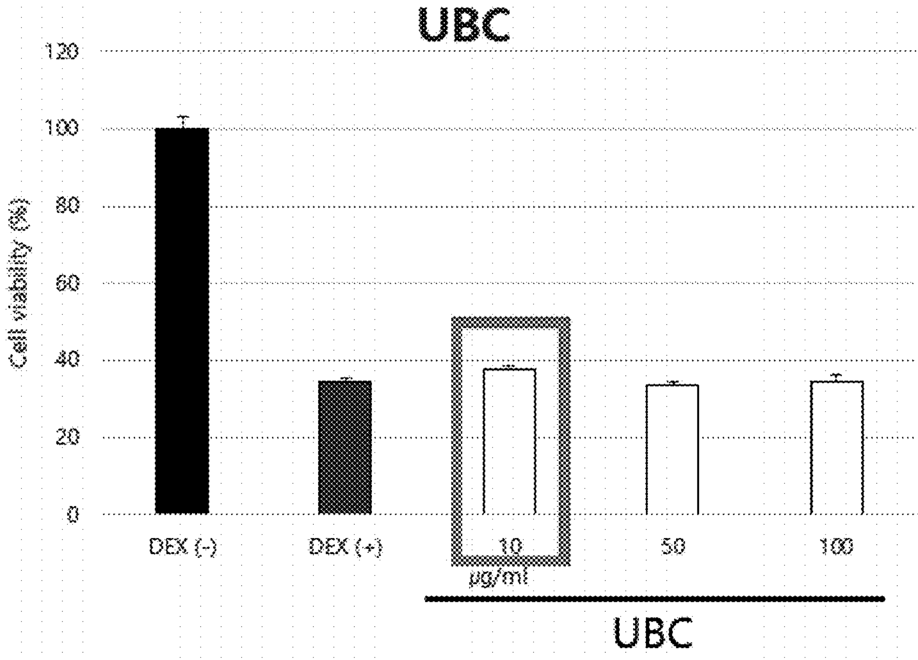

【FIG. 24】
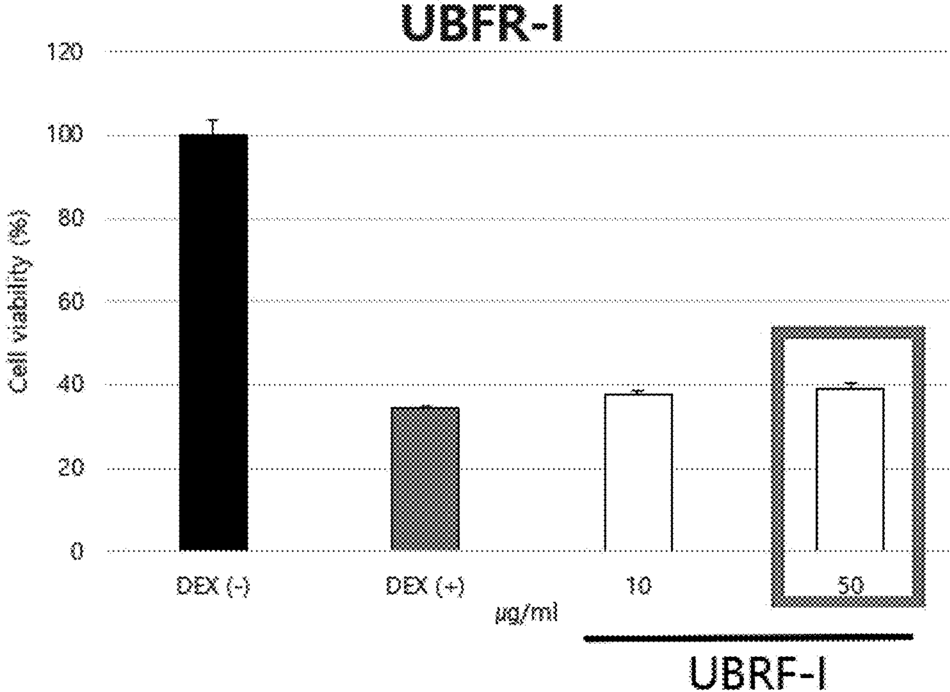
【FIG. 25】
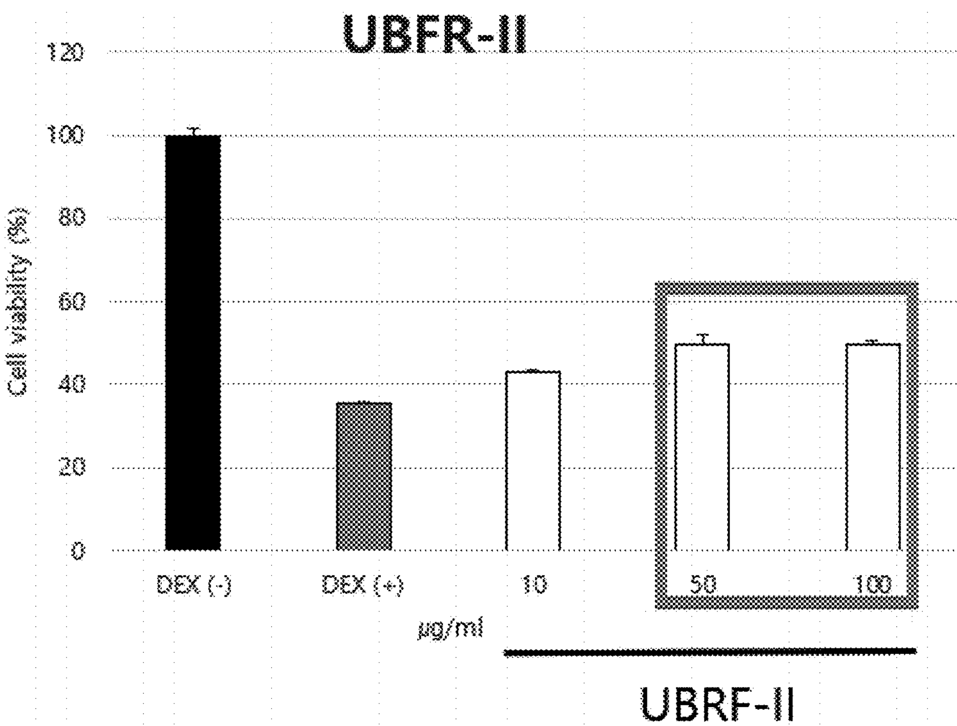

【FIG. 26】

| | | UR | UBC | UBRF-I | UBRF-II |
|---|---|---|---|---|---|
| DEX (-) | (-) | 100.0 ± 1.0 | 100.0 ± 3.0 | 100.0 ± 3.4 | 100.0 ± 1.6 |
| DEX (+) | (-) | 35.5 ± 1.1 | 34.3 ± 1.1 | 34.3 ± 0.5 | 35.4 ± 0.4 |
| DEX (+) | 10 μg/mL | 34.5 ± 0.7 | 37.5 ± 0.9 | 37.4 ± 1.0 | 43.1 ± 0.6 |
| DEX (+) | 50 μg/mL | 37.0 ± 1.0 | 33.4 ± 1.0 | 39.1 ± 1.4 | 49.7 ± 2.4 |
| DEX (+) | 100 μg/mL | 39.7 ± 0.6 | 34.5 ± 1.7 | - | 49.8 ± 1.0 |
| DEX (+) | 200 μg/mL | 41.2 ± 0.8 | - | - | - |

COMPOSITION FOR ANTI-OBESITY AND PREVENTING OR TREATING MUSCLE LOSS, CONTAINING CATECHIN GLYCOSIDE EXTRACT DERIVED FROM PLANT IN GENUS *Ulmus* AS ACTIVE INGREDIENT

CROSS-REFERENCE TO RELATED APPLICATIONS

This application is the U.S. National Phase under 35 U.S.C. § 371 of International Application No. PCT/KR2022/006674, filed on May 10, 2022, which in turn claims the benefit of Korean Applications No. 10-2022-0021852, filed on Feb. 21, 2022, and No. 10-2022-0037112, filed on Mar. 25, 2022, the disclosures of which are incorporated by reference into the present application.

TECHNICAL FIELD

The present disclosure relates to a composition for anti-obesity and preventing or treating muscle loss, which contains a catechin glycoside extract derived from a plant in the genus *Ulmus* as an active ingredient.

BACKGROUND ART

Lipid metabolism is necessary for the storage and distribution of energy in the body, regulation of glucose metabolism and maintenance of energy homeostasis. Abnormalities in lipid metabolism can cause the symptoms of obesity, diabetes, hyperlipidemia, etc. The lipid metabolism occurs mainly in liver and adipose tissues, and the lipid metabolism occurring in adipose tissues is regulated by adipocytes constituting the tissues. Adipocytes play important roles in metabolism. They not only store energy but also secrete several hormones and play active roles in metabolic processes.

Obesity is induced when the amount of triglycerides in adipocytes is increased or the number of the adipocytes is increased. Accordingly, it is necessary to reduce fat accumulation and decrease the number of adipocytes for prevention and treatment of obesity. In addition, since the adipocytes are differentiated from preadipocytes, the mechanism of adipogenesis is also very important to understand the role of adipose tissue. Recently, molecular biological studies on the differentiation and regulation of adipocytes that constitute adipose tissue have been conducted extensively. However, researches to elucidate their effects at the level of single compounds are insufficient.

Muscle can be divided into skeletal muscle, smooth muscle and cardiac muscle in terms of structure and function. Among them, the skeletal muscles are more than 600 voluntary muscles that lie under the skin of hands, feet, chest, abdomen, etc. and are attached to bones throughout the body through tendons. They are suitable for moving or supporting bones through contraction. The contraction is caused and regulated by nerve signals. They account for 40-50% of body weight and function to maintain body temperature, produce energy, etc. Because they consist of regularly arranged actin and myosin filaments, transverse patterns can be observed under a microscope (Lieber R. L., 2002; Edwards R. H., 1981).

Skeletal muscle fibers are biochemically classified into type I, type IIa and type IIb depending on their mitochondrial contents. The postural muscle that consists of red slow-twitch fibers and maintains posture by maintaining weak force for a long time is called type I. The muscle is suitable for aerobic exercise such as long-distance running due to its high mitochondrial content. The fast-twitch muscle having the features of the slow-twitch muscle is called type IIa. When making movements, muscle made of white fast-twitch fibers called active muscle is used and it is classified as type IIb. The muscle is suitable for anaerobic exercise such as short-distance running due to its low mitochondrial content. The muscle is distributed in different body parts with different skeletal muscle fibers (Tortora et al, 2008).

Muscle atrophy is caused by imbalanced anti-anabolic and catabolic actions of muscle fibers. The muscle atrophy refers to the loss of the size and mass of muscle cells and tissues caused by decreased activity due to aging, diseases conditions (excessive exposure to stress hormones, cancer, sepsis, starvation, etc.), bed rest, etc. When muscle atrophy occurs, the vicious cycle of weakening of muscle strength for physical activity and degeneration of the musculoskeletal system begins. Decreased walking speed, weakened grip strength, etc. are the main symptoms and indicators of muscle mass loss, and they can lead to falls, fractures, joint damage, metabolic disorders, cardiovascular diseases, etc.

Glucocorticoids are involved in anti-anabolic and catabolic actions directly or indirectly by causing molecular biological changes in muscle fibers. Dexamethasone, which is a glucocorticoid-based compound, inhibits the PI3K/Akt/mTOR pathway as an anti-anabolic action. It blocks the action of eIF4G (eukaryotic translation initiation factor 4 G) and eIF4E (eukaryotic translation initiation factor 4 E) by inhibiting the activity of downstream effectors such as 4E-BP1, S6K1, etc. This inhibits the translation of mRNA for protein synthesis, leading to atrophy of muscle fibers caused by inhibited muscle fiber synthesis and degradation of proteins (Shackman et al., 2013).

Dexamethasone induces muscle atrophy by inhibiting muscle synthesis and causing protein degradation. Atrogenes (atrogin-1 and MuRF-1) that induce muscle atrophy according to the mechanism of 'PI3K/Akt→FOXO activation and GSK3 inactivation' are expressed and these genes induce the degradation of proteins represented by the ubiquitin-proteasome system.

Therefore, it is necessary to develop a material for anti-obesity, which is cable of inhibiting muscle loss and degrading fats.

DISCLOSURE

Technical Problem

The present disclosure is directed to providing an extract having superior anti-obesity effect and muscle cell loss-preventing effect and a compound obtained therefrom.

Technical Solution

The present disclosure provides a pharmaceutical composition for anti-obesity and preventing or treating muscle loss, which contains an extract of a plant in the genus *Ulmus* as an active ingredient.

In an exemplary embodiment of the present disclosure, the extract of a plant in the genus *Ulmus* is an extract of a supercritical extract residue of a plant in the genus *Ulmus*.

In an exemplary embodiment of the present disclosure, the extract of a plant in the genus *Ulmus* is an alcohol extract of the branch or root of elm, and the extract of a supercritical extract residue of a plant in the genus *Ulmus* is prepared by a method including: (a) a step of obtaining a supercritical extract residue through supercritical extraction of a plant in the genus *Ulmus*; and (b) a step of obtaining an extract of the obtained supercritical extract residue of the plant in the genus *Ulmus*.

In an exemplary embodiment of the present disclosure, the extract is extracted using an ethanol solvent.

In an exemplary embodiment of the present disclosure, the extract of a plant in the genus *Ulmus* contains catechin 7-O-β-D-apiofuranoside.

The present disclosure also provides a functional health food for anti-obesity and preventing or alleviating muscle loss, which contains an extract of a plant in the genus *Ulmus* as an active ingredient.

In an exemplary embodiment of the present disclosure, the extract of a plant in the genus *Ulmus* is an extract of a supercritical extract residue of a plant in the genus *Ulmus*.

In an exemplary embodiment of the present disclosure, the extract of a plant in the genus *Ulmus* is an alcohol extract of the branch or root of elm.

In an exemplary embodiment of the present disclosure, the extract of a supercritical extract residue of a plant in the genus *Ulmus* is prepared by a method including: (a) a step of obtaining a supercritical extract residue through supercritical extraction of a plant in the genus *Ulmus*; and (b) a step of obtaining an extract of the obtained supercritical extract residue of the plant in the genus *Ulmus*.

In an exemplary embodiment of the present disclosure, the extract is extracted using an ethanol solvent.

In an exemplary embodiment of the present disclosure, the extract of a plant in the genus *Ulmus* contains catechin 7-O-β-D-apiofuranoside.

The present disclosure provides a feed for anti-obesity and preventing or alleviating muscle loss, which contains an extract of a plant in the genus *Ulmus* as an active ingredient, wherein the extract of a plant in the genus *Ulmus* contains catechin 7-O-β-D-apiofuranoside.

Advantageous Effects

A composition for anti-obesity and preventing or treating muscle loss according to the present disclosure exhibits the effect of inhibiting muscle loss caused by hydrogen peroxide or dexamethasone, based on an extract of a plant in the genus *Ulmus* and catechin glycoside contained in the extract.

In particular, it was identified that "catechin 7-O-β-D-apiofuranoside" elucidated as the effective indicator material of the plant in the genus *Ulmus* inhibits the differentiation of adipocytes in a concentration-dependent manner with statistical significance and inhibits adipocyte differentiation by 40% or more at the concentration of 20 μg/mL. Accordingly, the composition according to the present disclosure can be used as a key ingredient of a therapeutic agent or a functional food for anti-obesity and treating muscle loss.

BRIEF DESCRIPTION OF DRAWINGS

FIG. 1 describes extraction according to an exemplary embodiment of the present disclosure.

FIGS. 2 and 3 describes extraction of alcohol extracts of the branch and root of elm (UR and U60E).

FIG. 4 shows the TLC analysis result for UBRFI and UBRFII which are elm extracts prepared according to an exemplary embodiment of the present disclosure.

FIG. 5 shows the TLC analysis result for extracts of the branch and root of elm.

FIG. 6 shows the analysis result for catechin glycoside for U60E, UBC, UBRFI and UBRFIII.

FIG. 7 shows a result of investigating the degree of staining of adipocytes.

FIGS. 8 and 9 show the antioxidant activity analysis result in Test Example 4.

FIGS. 10 and 11 show the radical-scavenging activity analysis result in Test Example 5.

FIGS. 12-16 show the result of investigating cell viability for different samples.

FIGS. 17-21 show the result of investigating the effect of different samples on muscle cells damaged by $H_2O_2$.

FIGS. 22-26 show the result of investigating the effect of different samples on muscle cells damaged by dexamethasone.

BEST MODE

Hereinafter, specific exemplary embodiments of the present disclosure will be described referring to drawings. However, they are merely exemplary embodiments and the present disclosure is not limited thereby.

In the description of the present disclosure, a detailed description of a known technology will be omitted if it is determined that it may unnecessarily obscure the present disclosure. And, the terms used in the present disclosure, which are defined in consideration of functions in the present disclosure, may vary depending on the intention, practice, etc. of users or operators. Therefore, definition should be made based on the contents throughout the present specification.

The technical idea of the present disclosure is determined by the appended claims, and the following exemplary embodiments are provided merely as means for effectively explaining the technical idea of the present disclosure to those having ordinary knowledge in the art to which the present disclosure belongs. The present disclosure provides an anti-obesity composition containing an extract of a plant in the genus *Ulmus* as an active ingredient.

The anti-obesity composition according to an exemplary embodiment of the present disclosure contains "catechin 7-O-β-D-apiofuranoside" and has an effect of inhibiting adipocyte differentiation in a concentration-dependent manner.

The extract according to an exemplary embodiment of the present disclosure may be prepared by a method including: (a) a step of obtaining a supercritical extract residue through supercritical extraction of a plant in the genus *Ulmus*; and (b) a step of obtaining an extract of the obtained supercritical extract residue of the plant in the genus *Ulmus*.

Step (a): Obtainment of Supercritical Extract Residue Through Supercritical Extraction of Plant in Genus *Ulmus*

In the present disclosure, the supercritical extract residue of the plant in the genus *Ulmus* refers to a residue remaining after supercritical extraction of a plant in the order Rosales.

The plant in the genus *Ulmus* used to prepare the supercritical extract residue of the present disclosure includes plants in the genus *Ulmus* of the family Ulmaceae, and may be, for example, *Ulmus davidiana, Ulmus davidiana* var. *japonica, Ulmus davidiana* var. *japonica* for. *Suberosa, Ulmus parvifolia, Ulmus pumila, Ulmus laciniata, Ulmus macrocarpa*, etc. Specifically, *Ulmus davidiana* var. *japonica, Ulmus macrocarpa* or *Ulmus davidiana* may be used, although not being limited thereto.

The plant in the genus *Ulmus* may be the whole plant of the plant in the genus *Ulmus* or a part of the plant in the genus *Ulmus*, which is one or more selected from a group consisting of branch, stem, root, leaf, flower, fruit and seed.

Specifically, the branch, stem or root of the plant in the genus *Ulmus* may be used, although not being limited thereto.

In the present disclosure, the whole plant or part of the plant in the genus *Ulmus* may be dried and/or ground before the supercritical extraction.

In the present disclosure, the supercritical extraction refers to a method of extracting a flavorant, pigment, oil or functional substance contained in a natural product using a fluid in supercritical state.

The fluid in supercritical state refers to a fluid which is in a state of a temperature and a pressure above its supercritical point, where distinct gas and liquid phases do not exist. The supercritical fluid may be, for example, supercritical carbon dioxide. The supercritical carbon dioxide is a fluid state of carbon dioxide above its critical temperature (31° C.) and critical pressure (7.5 MPa) where it has the properties of gas and liquid at the same time.

In the present disclosure, the supercritical extraction may be performed by, for example, by a pressure variation method wherein a mixture of a supercritical fluid and a solute is swollen under reduced pressure at extraction temperature, so that the solute is separated as the solvent power of the supercritical fluid is decreased, or a temperature variation method wherein a supercritical fluid and a solute are separated as the solvent power of the supercritical fluid is decreased by increasing temperature, although not being limited thereto.

In the present disclosure, a cosolvent may be used together with the supercritical fluid. The cosolvent includes a polar solvent commonly used in the art and may be specifically selected from a group consisting of an alcohol, water, ethylene glycol, polyethylene glycol, propylene carbonate, formic acid, acetic acid, acetonitrile, chlorodifluoromethane and mixtures thereof.

In the present disclosure, a vessel used for the supercritical extraction is not particularly limited as long as the control of temperature and pressure is possible and the raw material to be extracted can be contacted with a supercritical fluid.

In the present disclosure, the supercritical extraction may be performed at a pressure of 100-600 bar and at a temperature of 10-100° C. During the supercritical extraction, the flow rate of the supercritical fluid and the cosolvent may be 10-100 g/min. The pressure, temperature and the flow rate of the supercritical fluid and the cosolvent during the supercritical extraction may be adequately adjusted by those having ordinary skill in the art in the above ranges.

After the supercritical extraction of the plant in the genus *Ulmus*, the remaining supercritical extract residue is collected and used as a raw material for the following solvent extraction.

Step (b): Obtainment of Extract of Supercritical Extract Residue of Plant in Genus *Ulmus*

In the step (b), an extract of a supercritical extract residue of a plant in the genus *Ulmus* is obtained through solvent extraction of the supercritical extract residue of the plant in the genus *Ulmus*.

In the present specification, the term "extract" used referring to the extract of a supercritical extract residue of a plant in the genus *Ulmus* includes not only an extract obtained by treating a plant in the genus *Ulmus* supercritical extract residue with an extraction solvent but also a processed extract (e.g., powder) formulated for administration of the extract of a supercritical extract residue of a plant in the genus *Ulmus* to a subject.

The extract of a supercritical extract residue of a plant in the genus *Ulmus* of the present disclosure may be separated by a common method for extracting from a natural product known in the art, for example, under common temperature and pressure conditions using a common solvent.

A variety of extraction solvents may be used to obtain an extract of the supercritical extract residue of the plant in the genus *Ulmus*. Specifically, a polar solvent or a nonpolar solvent may be used. Suitable polar solvents include (i) water, (ii) an alcohol (e.g., methanol, ethanol, propanol, butanol, n-propanol, isopropanol, n-butanol, 1-pentanol, 2-butoxyethanol or ethylene glycol), (iii) acetic acid, (iv) DMF (dimethylformamide) and (v) DMSO (dimethyl sulfoxide). Suitable nonpolar solvents include acetone, acetonitrile, ethyl acetate, methyl acetate, fluoroalkane, pentane, hexane, 2,2,4-trimethylpentane, decane, cyclohexane, cyclopentane, diisobutylene, 1-pentene, 1-chlorobutane, 1-chloropentane, o-xylene, diisopropyl ether, 2-chloropropane, toluene, 1-chloropropane, chlorobenzene, benzene, diethyl ether, diethyl sulfide, chloroform, dichloromethane, 1,2-dichloroethane, aniline, diethylamine, ether, carbon tetrachloride and THF (tetrahydrofuran).

More specifically, the extraction solvent used in the present disclosure includes (a) water, (b) an alcohol, (c) a mixed solvent of a lower alcohol and water, (d) acetone, (e) ethyl acetate, (f) chloroform, (g) butyl acetate, (h) 1,3-butylene glycol, (i) hexane and (j) diethyl ether.

In an exemplary embodiment, the alcohol may be a $C_{1-4}$ anhydrous or hydrous lower alcohol (methanol, ethanol, propanol, butanol, n-propanol, isopropanol, n-butanol, etc.), specifically ethanol.

In another exemplary embodiment, the ethanol may be specifically 10-90% ethanol, more specifically 20-80%, further more specifically 30-80%, 40-70%, 50-70% or 55-65% ethanol, most specifically 60% ethanol.

In another exemplary embodiment, the extract of the present disclosure may include a fraction obtained by fractionating the solvent extract using a solvent.

Specifically, the solvent extraction is performed by contacting the supercritical extract residue of the plant in the genus *Ulmus* with an extraction solvent. Specifically, the extraction using an extraction solvent may be adequately selected by those skilled in the art by one or more method selected from a group consisting of room temperature extraction, hot water extraction, cold extraction, reflux extraction, microwave extraction and ultrasonic extraction.

In the present disclosure, the extraction solvent may be removed partially or completely after the solvent extraction through a filtration, concentration or drying process. The partial removal refers to concentration until an aqueous concentrate with a considerable amount of the organic solvent removed is obtained, and a dry residue may be obtained through the complete removal. For example, the filtration may be performed using a filter paper or a vacuum filter, the concentration may be performed using a vacuum concentrator, and the drying may be performed by freeze-drying, etc., although not being limited thereto.

In the present disclosure, the term "extract" refers to a crude extract commonly used in the art but also includes, in a broad sense, a fraction obtained by additionally fractionating the crude extract. The fractionation using a solvent may be performed by an additional extraction process using the solvent.

In the present disclosure, the extract of a supercritical extract residue of a plant in the genus *Ulmus* contains catechin 7-O-β-D-apiofuranoside, which is a catechin glycoside represented by Chemical Formula 1.

[Chemical Formula 1]

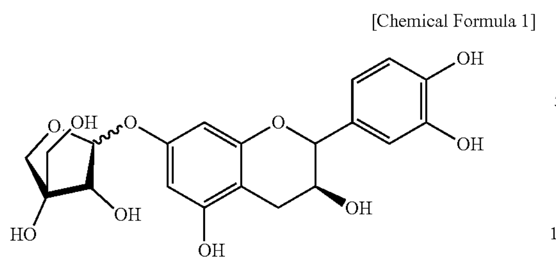

In the present disclosure, the extract of a supercritical extract residue of a plant in the genus *Ulmus* may contain the catechin 7-O-β-D-apiofuranoside at a content of 10-200 μg/mL, more specifically 40-200 μg/mL, 50-190 μg/mL, 60-190 μg/mL, 60-180 μg/mL, 70-180 μg/mL, 80-180 μg/mL, 80-170 μg/mL, 90-170 μg/mL, 90-160 μg/mL, 100-160 μg/mL, 100-150 μg/mL or 100-140 μg/mL. The compound of Chemical Formula 1 may also be used as an active ingredient of an anti-obesity pharmaceutical composition, which is included in the scope of the present disclosure.

In the present specification, the expression "containing as an active ingredient" means that the compound is contained in an amount sufficient to achieve the anti-obesity effect of the extract of the present disclosure, which can be confirmed from the effect of inhibiting adipocyte differentiation.

The anti-obesity pharmaceutical composition of the present disclosure may further contain a pharmaceutically acceptable carrier, excipient or diluent.

In the composition of the present disclosure, the pharmaceutically acceptable carrier includes those commonly used for formulation such as lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc., although not being limited thereto. The pharmaceutical composition of the present disclosure may further contain, in addition to the above-described ingredients, a lubricant, a wetting agent, a sweetener, a flavorant, an emulsifier, a suspending agent, a preservative, etc. Suitable pharmaceutically acceptable carriers and preparations are described in detail in Remington's Pharmaceutical Sciences (19th ed., 1995).

The pharmaceutical composition of the present disclosure may be administered orally or parenterally. For parenteral administration, the pharmaceutical composition may be administered by intravenous injection, subcutaneous injection, subcutaneous injection, intramuscular injection, intraperitoneal injection, transdermal administration, etc.

An appropriate administration dosage of the pharmaceutical composition of the present disclosure varies depending on such factors as formulation method, administration method, the age, body weight, sex, pathological condition and diet of a patient, administration time, administration route, excretion rate and response sensitivity. An ordinarily skilled physician can easily determine and prescribe an administration dosage effective for the desired treatment or prevention.

The anti-obesity pharmaceutical composition of the present disclosure may contain another pharmaceutically active ingredient in addition to the extract of a plant in the genus *Ulmus* as an active ingredient, or may be used together with a pharmaceutical composition containing another active ingredient.

The present disclosure also provides a composition for preventing or alleviating muscle loss, which contains an extract of a supercritical extract residue of a plant in the genus *Ulmus* as an active ingredient.

A food or functional health food composition of the present disclosure may further contain a sitologically acceptable food additive. The sitologically acceptable food additive that may be used in the present disclosure may be selected from a group consisting of a natural carbohydrate such as a sugar such as glucose, fructose, maltose, sucrose, dextrin and cyclodextrin or a sugar alcohol such as xylitol, sorbitol, erythritol, etc., a natural flavorant such as thaumatin, stevia extract, etc., a synthetic flavorant such as saccharine, aspartic acid, a colorant, pectic acid or its salts, alginic acid or its salts, an organic acid, a protective colloidal thickener, a pH control agent, a stabilizer, an antiseptic, glycerin, an alcohol, a carbonating agent, etc., although not being limited thereto. The food composition of the present disclosure may be in a form selected from a group consisting of a powder, a granule, a tablet, a capsule, a candy, a chewing gum, a jelly and a beverage. The content of the extract of a plant in the genus *Ulmus* in the food composition may be selected adequately in consideration of the form, flavor, taste, etc. of the food, and may be, for example, 0.01-30 wt % based on the total weight of the food. It will be obvious to those having ordinary skill that the form, composition, preparation method, etc. of the food composition according to the present disclosure can be selected adequately from the common technology known in the art.

The anti-obesity food composition of the present disclosure contains 7-O-β-D-apiofuranoside, which is a catechin glycoside represented by Chemical Formula 1.

A detailed description will be omitted since it is the same as that described above.

EXAMPLES

Supercritical Extraction

FIG. 1 describes extraction according to an exemplary embodiment of the present disclosure.

Hereinafter, an extraction method according to the present disclosure will be described in detail referring to FIG. 1.

A supercritical fluid extraction apparatus (ISA-SEFE-0500-0700-080, IlsinAutoclave, Daejeon, Korea) was used to obtain an elm-derived extract. After removing impurities from a sample, followed by washing, the sample was dried in the shade and used as an experimental material. After pulverizing 100 g of a dried elm bark sample to pass through a 200-mesh sieve, the sample was put in an extraction tank maintained at 40-60° C.

After the temperature was stabilized, $CO_2$ gas maintained was injected using a high-pressure pump through a line until the pressure reached 400-600 bar. After the set pressure was reached, extraction was conducted by adding ethanol to the extraction tank at a rate of 5 mL/min or 10 mL/min for 60 minutes or 240 minutes. In order to remove the ethanol remaining in the sample, $CO_2$ was flown at preset pressure and temperature for 30 minutes using a high-pressure pump. The lab-scale supercritical fluid extraction apparatus used in the experiment is schematically shown in FIG. 1. The lab-scale extraction apparatus consists of an extraction tank for supplying carbon dioxide, a separation tank, a heat exchanger, high-pressure pump, etc.

Solvent Fractionation

The elm supercritical extract residue obtained after the supercritical extraction was recovered and extracted in ethanol (60%) at room temperature for 7 days. Then, a final elm supercritical extract residue alcohol extract (UBRFI) was obtained through filtration using a filter paper, concentration under reduced pressure and freeze-drying. After dissolving the obtained primary extract, UBRFI, in distilled water (singly or triply distilled water) and filtering using a filter paper, an ethyl acetate (EtOAC) layer was obtained using a separatory funnel. The obtained secondary extract is an elm-derived high-content extract (UBRFII).

Branch and Root Alcohol Extracts

Alcohol extracts were prepared from the root and branch samples of elm.

For the elm root extract, the root (6.45 kg) was extracted at room temperature with 60% ethanol and filtered through a filter paper. The extract (UR, 392 g) was recovered through concentration under reduced pressure. Thin-layer chromatography (TLC) was conducted using a mixture of chloroform, methanol and water (70:30:4) as an eluent and the presence of catechin-7-O-β-D-apiofuranoside was identified. In addition, the content of the catechin glycoside was identified through quantitative HPLC analysis.

For the elm branch extract, the branch (10 kg) was extracted at room temperature with 60% ethanol and filtered through a filter paper. The extract (U60E, 429 g) was recovered through concentration under reduced pressure. Thin-layer chromatography (TLC) was conducted using a mixture of chloroform, methanol and water (70:30:4) as an eluent and the presence of catechin-7-O-β-D-apiofuranoside was identified. In addition, the content of the catechin glycoside was identified through quantitative HPLC analysis.

Test Example 1

Analysis of Compounds

The marker compounds in the elm extract were analyzed by NMR and MS. The analysis result is as follows and the catechin-7-O-β-D-apiofuranoside of Chemical Formula 1 could be identified.

High-resolution TOF-MS m/z: 422.17511 $[M]^+$; $^1$H-NMR (400 MHZ, DMSO-$d_6$+$D_2O$): 6.74 (H-2', 1H, d, J=2.0 Hz), 6.69 (H-5', 1H, d, J=8.4 Hz), 6.59 (H-6', 1H, dd, J=2.0, 8.4 Hz), 6.09 (H-8, 1H, d, J=2.4 Hz), 5.90 (H-6, 1H, J=2.4 Hz), 5.33 (H-1", 1H, d, J=4.0 Hz), 4.55 (H-2, 1H, d, J=7.2 Hz), 4.03 (H-2", 1H, d, J=4.0 Hz), 4.00 (H-4a", 1H, d, J=9.6 Hz), 3.89 (H-3, 1H, m), 3.68 (H-4b", 1H, d, J=9.6 Hz), 3.45 (H-5", 2H, m), 2.65 (H-4a, 1H, dd, J=4.8, 16.0 Hz), 2.40 (H-4b, 1H, dd, J=8.0, 16.0 Hz); $^{13}$C-NMR (100 MHz, DMSO-$d_6$+$D_2O$): δ 156.7 (C-7), 156.5 (C-5), 155.7 (C-9), 145.2 (C-4'), 145.1 (C-3'), 130.8 (C-1'), 118.8 (C-6'), 115.6 (C-5'), 114.7 (C-2'), 107.3 (C-1"), 102.1 (C-10), 96.0 (C-8), 95.3 (C-6), 81.4 (C-2), 78.9 (C-3"), 76.3 (C-2"), 74.3 (C-4"), 66.3 (C-3), 62.4 (C-5"), 27.8 (C-4).

TLC Analysis

FIG. 4 shows the TLC analysis result for UBRFI and UBRFII which are the elm extracts prepared by the method described above. A mixture of chloroform, MeOH and water (70:30:4) was used as an eluent. The left, center and right columns indicate catechin-7-O-β-D-apiofuranoside, UBRFI and UBRFII, respectively.

Referring to FIG. 4, the presence of the catechin glycoside in UBRFI and UBRFII was identified through the TLC analysis.

FIG. 5 shows the TLC analysis result for the extracts of the branch and root of elm. A mixture of chloroform, MeOH and water (70:30:4) was used as an eluent. The left, center and right columns indicate catechin-7-O-β-D-apiofuranoside, UBRFI and UBRFII, respectively.

Referring to FIG. 5, the presence of the catechin glycoside in UR and U60E was identified.

Test Example 2

HPLC Analysis

HPLC analysis was conducted using a Waters 2695 Separation module, a 2487 Dual λ absorbance detector, a SkyPak C18 analytical column (5 μm) and a Phenomenex KJ0-4282 guard column. 0.9% acetic acid (A) and ACN (B) were used as mobile phases (gradient program: 5% B 0 min, 10% B 0-5 min, 15% B 5-7 min, 25% B 7-30 min, 5% B 30-31 min, 5% B 31-35 min).

FIG. 6 shows the analysis result for the catechin glycoside for U60E, UBC, UBRFI and UBRFIII.

Referring to FIG. 6, it was identified that the catechin content was increased by about 3 times for UBRF-I and by 10 times or more for UBRF-II as compared to UR, which is a conventional elm 60% alcohol extract. In addition, it was confirmed that the content of the catechin glycoside in UBC, which is an elm bark 60% alcohol extract, was approximately 2 times higher than UR. Accordingly, the catechin content is higher in the order of UBRF-II, UBRF-I, UBC and UR.

Test Example 3

Test of Adipocyte Differentiation-Inhibiting Ability

1. Cell Culturing

3T3-L1 cells, which are mouse-derived preadipocytes, were purchased from Korean Cell Line Bank. The 3T3-L1 cells were cultured using an DMEM medium (Welgene) supplemented with 10% bovine calf serum (BCF), 100 units/mL penicillin and 100 μg/mL streptomycin (complete DMEM medium) in a humidified $CO_2$ incubator (5% $CO_2$/95% air) at 37° C. When the cells filled about 80% of the culture dish, the cell monolayer was washed with phosphate-buffered saline (PBS, pH 7.4) and the cells were detached by adding trypsin-2.65 mM EDTA. Then, the cells were subcultured while replacing the medium every other day.

2. Measurement of Cell Viability

3T3-L1 cells were seeded onto a 24-well plate at $3\times10^4$ cells/well and cultured for 24 hours. Then, the cells were cultured for 72 hours after exchanging the medium with one containing the test substance. After the culturing for 72 hours, the number of living cells were counted by MTT assay (Denizot F and Lang R. *J Immunological Method* 89:271-277, 1986). The MTT assay is based on the principle that mitochondrial dehydrogenase reduces MTT (Amresco) to form blue formazan. The formazan was dissolved in isopropanol and then absorbance was measured at a wavelength of 570 nm.

3. Induction of Differentiation and Treatment With Test Substance

3T3-L1 cells were seeded onto a 24-well plate at $1\times10^5$ cells/well. When the cells reached confluence, differentiation into adipocytes was induced by culturing the cells while replacing the medium sequentially with three differentiation media (DM). That is to say, differentiation was induced for 2 days by replacing the medium with a differentiation medium wherein DMI (1 μM dexamethasone, 0.5 mM 3-isobutyl-1-methylxanthine (IBMX) and 5 μg/mL insulin) was added to a DMEM medium containing 10% FBS. Then, differentiation was induced again for 2 days by replacing the medium with a fresh differentiation medium wherein 5 μg/mL insulin was added to a DMEM medium containing 10% FBS. Then, differentiation into adipocytes was induced by maintaining the cells for 2 days in a DMEM medium containing 10% FBS.

In order to investigate the effect of the test substance on adipocyte differentiation, the test substance was added in the differentiation medium and treated to the cells.

4. Measurement of Adipocyte Differentiation (Fat Accumulation) (Oil Red O Staining)

After treating with the test substance while inducing the differentiation of the 3T3-L1 cells, the cells were rinsed with DPBS (Welgene) and then fixed at room temperature by putting in 4% paraformaldehyde (PFA, Biosesang) for 1 hour. Then, the cells were stained by treating with Oil Red O (Sigma-Aldrich) at room temperature for 1-2 hours. After visually identifying the degree of staining of adipocytes, the cells were rinsed with distilled water and the adipocytes were observed under a microscope.

FIG. 7 shows the result of investigating the degree of staining of adipocytes.

Referring to FIG. 7, it was confirmed that the treatment with "catechin 7-O-β-D-apiofuranoside" of Chemical Formula 1, which was identified as the marker compound and active ingredient of the extract of the plant in the genus *Ulmus*, resulted in statistically significant adipocyte differentiation-inhibiting ability in a concentration-dependent manner. In particular, the adipocyte differentiation-inhibiting ability was 40% or higher at the concentration of 20 μg/mL, which was the highest concentration tested.

This result suggests that the extract of the plant in the genus *Ulmus* containing "catechin 7-O-β-D-apiofuranoside" can be developed into a raw material for an anti-obesity therapeutic agent or functional food.

Test Example 4

Analysis of Antioxidant Activity

For analysis of DPPH radical-scavenging ability, 20 μL of a sample and 180 μL of a 1 mM DPPH reagent were reacted for 30 minutes in the dark in a 96-well plate. After the reaction, absorbance was measured at 517 nm using an ELISA reader.

FIGS. 8 and 9 show the antioxidant activity analysis result in Test Example 4.

Referring to FIGS. 8 and 9, all the samples showed radical-scavenging ability in a concentration-dependent manner. They showed DPPH radical-scavenging ability comparable to that of vitamin C, which was used as a positive control. In particular, UBC exhibited higher radical-scavenging ability than other samples. UBC showed the highest $IC_{50}$ value.

Test Example 5

Analysis of ABTS Radical-Scavenging Activity

In this test example, for analysis ABTS radical-scavenging ability, radicals were produced by mixing 2.45 mM potassium persulfate and 7.0 mM ABTS at a ratio of 1:1 and conducting reaction for 24 hours in the dark. The reaction mixture was diluted with a PBS buffer so that absorbance was between 0.7 and 1.0. After reacting 20 μL of a sample and 180 μL of an ABTS reagent for 15 minutes in a 96-well plate in the dark, absorbance was measured at 750 nm using an ELISA reader.

FIGS. 10 and 11 show the radical-scavenging activity analysis result in Test Example 5.

Referring to FIGS. 10 and 11, all the samples showed ABTS radical-scavenging ability in a concentration-dependent manner. In addition, three samples showed high scavenging ability at low concentrations and, particularly, all the samples showed radical-scavenging ability comparable to that of vitamin C at 250 μg/mL. UBC and UBRF-II showed the highest $IC_{50}$ values.

Test Example 6

Analysis of Cytotoxicity

In order to evaluate the fat-degrading ability and muscle loss-preventing effect of the natural product extracts (UR, UBC, UBRF-I and UBFF-II), the effect of protection against $H_2O_2$— and dexamethasone-induced muscle cell damage was investigated in vitro. All analysis results were represented as mean±SEM and the collected data were analyzed using the GraphPad Prism 5.0 (GraphPad software, San Diego, CA, USA) program. The difference between a control group and test substance treatment groups was compared by Student's t-test and one-way analysis variance (ANOVA). $P<0.05$ was considered statistically significant.

UR, UBC, UBRF-I and UBFF-II were used as samples. C2C12 cells, which are myoblasts derived from mouse skeletal muscle, were purchased from American Type Culture Collection (ATCC). The C2C12 cells were cultured using a cell culture medium wherein 10% fetal bovine serum (FBS), 100 units/mL penicillin and 100 μg/ml streptomycin were added to Dulbecco's modified Eagle's medium (DMEM) in a humidified $CO_2$ incubator (5% $CO_2$/95% air) at 37° C. When the cells filled about 80% of the culture dish, the cell monolayer was washed with phosphate-buffered saline (PBS, pH 7.4) and the cells were detached by adding trypsin-2.65 mM EDTA. Then, the cells were subcultured while replacing the medium every other day.

Analysis of Cell Viability

The cell viability of C2C12 cells was measured by MTT assay (Denizot F and Lang R. *J Immunological Method* 89:271-277, 1986). C2C12 cells were seeded onto a 24-well plate at $2.5\times10^4$ cells/well and cultured for 24 hours. Then, the cells were cultured for 24 hours after exchanging the medium with one containing the test substance at various concentrations (0, 10, 50, 100, 150 and 200 μg/mL). After the culturing for 24 hours, the cells were cultured for 2 hours after exchanging the medium with one containing 1 mg/mL MTT (Amresco). Then, the formazan formed from living cells was dissolved in isopropanol and absorbance was measured at a wavelength of 570 nm.

Analysis of Protective Effect Against $H_2O_2$-Induced Muscle Cell Damage

C2C12 cells were seeded onto a 24-well plate at $2.5\times10^4$ cells/well and cultured for 24 hours. Then, the cells were treated with 100 μM $H_2O_2$ to induce muscle cell damage and then cultured for 24 hours after treating with the test substance at various concentrations in order to investigate the protective effect of the test substance against muscle cell damage. After the culturing for 24 hours, cell viability was measured by MTT assay.

Analysis of Protective Effect Against Dexamethasone-Induced Muscle Cell Damage

C2C12 cells were seeded onto a 24-well plate at $2.5\times10^4$ cells/well and cultured for 24 hours. Then, the cells were treated with 500 μM dexamethasone to induce muscle cell damage and then cultured for 24 hours after treating with the test substance at various concentrations in order to investigate the protective effect of the test substance against muscle cell damage. After the culturing for 24 hours, cell viability was measured by MTT assay.

Analysis of Effect of Natural Product Extracts (UR, UBC, UBRF-I and UBFF-II) on Cell Viability FIGS. 12-16 show the result of investigating cell viability for the different samples.

Referring to FIGS. 12-16, the cell viability of the C2C12 cells was increased by the treatment of UR, UBC, UBRF-I and UBFF-II at various concentrations (10, 50, 100, 150 and 200 μg/mL). The treatment of UR increased the cell viability in a concentration-dependent manner. Especially, the cell viability was increased by 21% as compared to a control group (0 μg/mL) when UR was treated at a concentration of 200 μg/mL. The treatment of UBC at concentrations of 50 μg/mL and 100 μg/mL significantly increased the cell viability of the C2C12 cells as compared to the control group (0 g/mL). UBRF-I (10-200 μg/mL) had no cytotoxicity for the C2C12 cells, and UBRF-II increased the cell viability of the C2C12 cells in a concentration-dependent manner.

Analysis of Effect of Natural Product Extracts (UR, UBC, UBRF-I and UBFF-II) on $H_2O_2$-Induced Muscle Cell Damage $H_2O_2$ (hydrogen peroxide) is a strong oxidizer and induces oxidative stress in vitro. In order to investigate the effect of UR, UBC, UBRF-I and UBFF-II according to the present disclosure on muscle cell damage caused by oxidative stress, C2C12 cells were treated with 100 μM $H_2O_2$ to induce oxidative stress. Then, after treating the cells with UR, UBC, UBRF-I and UBFF-II and culturing them, the cell viability of the C2C12 cells was measured.

FIGS. 17-21 show the result of investigating the effect of the samples on muscle cells damaged by $H_2O_2$.

Referring to FIGS. 17-21, the treatment with $H_2O_2$ remarkably decreased cell viability as compared to a control group not treated with $H_2O_2$ [$H_2O_2$ (−)/(−)]. The treatment with UR (10, 50, 100 and 200 μg/mL) increased the cell viability in a concentration-dependent manner. At the highest concentration of 200 μg/mL, the cell viability was increased by 55.9% as compared to a control group treated with $H_2O_2$ only [$H_2O_2$ (+)/(−)].

The treatment with UBC (10, 50 and 100 μg/mL) significantly increased the cell viability as compared to the control group treated with $H_2O_2$ only. The treatment with UBRF-I increased the cell viability in a concentration-dependent manner as compared to the control group [$H_2O_2$ (+)/(−)], and the cell viability was increased by 38.2% as compared to the control group at the concentration of 100 μg/mL. UBRF-II had no significant effect on the cell viability of the C2C12 cells wherein oxidative stress was induced with $H_2O_2$ at 10, 50 and 100 μg/mL. However, when UBRF-II was treated at the concentration of 200 μg/mL, the cell viability was significantly decreased as compared to the control group treated with $H_2O_2$ only [$H_2O_2$ (+)/(−)].

Analysis of Effect of Natural Product Extracts (UR, UBC, UBRF-I and UBFF-II) on Dexamethasone-Induced Muscle Cell Damage Dexamethasone is one of representative glucocorticoids. Misuse or abuse of dexamethasone in clinical practice causes degradation of skeletal muscles. Therefore, it is widely used to induce muscle cell damage in vitro. In order to investigate the effect of UR, UBC, UBRF-I and UBFF-II on muscle cell damage caused by the glucocorticoid, C2C12 cells were treated with 500 μM dexamethasone to induce muscle cell damage and the cell viability of the C2C12 cells was measured after treating with UR, UBC, UBRF-I and UBFF-II and culturing them.

FIGS. 22-26 show the result of investigating the effect of the samples on muscle cells damaged by dexamethasone.

Referring to FIGS. 22-26, the treatment with dexamethasone remarkably decreased the cell viability as compared to a control group not treated with dexamethasone [DEX (−)/(−)].

The treatment with UR at concentrations of 100 and 200 μg/mL increased the cell viability as compared to a control group treated with dexamethasone only [DEX (+)/(−)]. UBC exhibited the protective effect against cell damage at 10 g/mL. The treatment with UBRF-I at low concentrations of 10 and 50 μg/mL increased the cell viability as compared to the control group [DEX (+)/(−)].

The treatment with UBRF-II at concentrations of 10, 50 and 100 μg/ml significantly increased the cell viability as compared to the control group [DEX (+)/(−)]. In particular, the treatment with UBRF-II at a concentration of 100 g/mL increased the cell viability by 40.7% as compared to the control group [DEX (+)/(−)], which confirms the protective effect against cell damage.

The invention claimed is:

1. A pharmaceutical composition for preventing or treating muscle loss, comprising, as an active ingredient, a secondary extract of a supercritical extract residue of a plant in the genus *Ulmus,* wherein the secondary extract is obtained by:

(a) subjecting a plant of the genus *Ulmus* to supercritical fluid extraction to obtain a supercritical extract residue;

(b) extracting the supercritical extract residue with an alcohol solvent to obtain an alcohol extract;

(c) filtering the alcohol extract and removing solvent therefrom to obtain a primary extract (UBRF-I); and (d) fractionating the primary extract with ethyl acetate to obtain the secondary extract (UBRF-II), wherein the secondary extract has a catechin 7-O-β-D-apiofuranoside content of at least 500 μg/mL, as determined by HPLC.

2. The pharmaceutical composition of claim 1, wherein the alcohol solvent is ethanol.

3. The pharmaceutical composition of claim 2, wherein the ethanol is 55-65% (v/v) ethanol.

4. The pharmaceutical composition of claim 1, wherein the plant of the genus *Ulmus* is selected from a branch, stem, root, or bark of the plant.

5. The pharmaceutical composition of claim 1, wherein the plant of the genus *Ulmus* is selected from the group consisting of *Ulmus davidiana, Ulmus davidiana* var. *japonica, Ulmus macrocarpa, Ulmus pumila, Ulmus parvifolia, Ulmus laciniata*, and combinations thereof.

6. The pharmaceutical composition of claim 1, wherein the catechin 7-O-β-D-apiofuranoside is a catechin glycoside represented by Chemical Formula 1,

[Chemical Formula 1]

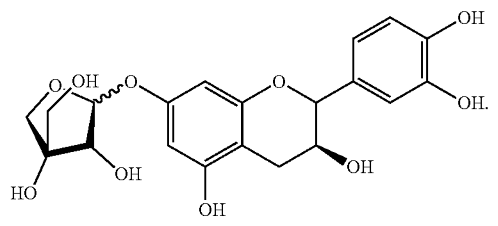

7. A functional health food for preventing or alleviating muscle loss, comprising, as an active ingredient, a secondary extract of a supercritical extract residue of a plant in the genus *Ulmus,* wherein the secondary extract is obtained by:

(a) subjecting a plant of the genus *Ulmus* to supercritical fluid extraction to obtain a supercritical extract residue;

(b) extracting the supercritical extract residue with an alcohol solvent to obtain an alcohol extract;

(c) filtering the alcohol extract and removing solvent therefrom to obtain a primary extract (UBRF-I); and (d) fractionating the primary extract with ethyl acetate to obtain the secondary extract (UBRF-II), wherein the secondary extract has a catechin 7-O-β-D-apiofuranoside content of at least 500 μg/mL, as determined by HPLC.

8. A method of preventing or treating muscle loss in a subject in need thereof, comprising administering to the subject a therapeutically effective amount of the pharmaceutical composition of claim 1.

9. The method of claim 8, wherein the pharmaceutical composition is administered orally or parenterally.

* * * * *